(12) United States Patent
Meyerhoff et al.

(10) Patent No.: US 8,168,423 B2
(45) Date of Patent: May 1, 2012

(54) DEVICE FOR DETECTING NITROSOTHIOL CONTENT IN SOLUTION

(75) Inventors: Mark E. Meyerhoff, Ann Arbor, MI (US); Wansik Cha, Ann Arbor, MI (US)

(73) Assignee: The Regents of The University of Michigan, Ann Arbor, MI (US)

( * ) Notice: Subject to any disclaimer, the term of this patent is extended or adjusted under 35 U.S.C. 154(b) by 1064 days.

(21) Appl. No.: 12/061,271

(22) Filed: Apr. 2, 2008

(65) Prior Publication Data

US 2010/0276284 A1    Nov. 4, 2010

Related U.S. Application Data

(60) Division of application No. 11/944,034, filed on Nov. 21, 2007, now Pat. No. 8,034,384, which is a continuation of application No. 10/794,878, filed on Mar. 5, 2004, now Pat. No. 7,335,383, which is a continuation-in-part of application No. 10/052,239, filed on Jan. 16, 2002, now Pat. No. 7,128,904.

(60) Provisional application No. 60/262,014, filed on Jan. 16, 2001.

(51) Int. Cl.
    C12M 1/34        (2006.01)
    C12Q 1/00        (2006.01)
(52) U.S. Cl. ......................... 435/287.1; 435/4
(58) Field of Classification Search .......................... None
    See application file for complete search history.

(56) References Cited

U.S. PATENT DOCUMENTS

| | | | |
|---|---|---|---|
| 3,933,589 A | 1/1976 | Keyes | |
| 4,339,448 A | 7/1982 | Dockner et al. | |
| 5,169,936 A | 12/1992 | Staples et al. | |
| 5,283,339 A | 2/1994 | Arnold et al. | |
| 5,294,539 A | 3/1994 | Johannssen et al. | |
| 5,386,012 A | 1/1995 | Strid | |
| 5,603,820 A * | 2/1997 | Malinski et al. | 205/781 |
| 5,626,738 A * | 5/1997 | Richie | 205/444 |
| 5,824,673 A | 10/1998 | Abrams et al. | |
| 5,834,030 A | 11/1998 | Bolton | |
| 5,858,792 A | 1/1999 | Fanning et al. | |
| 5,990,289 A | 11/1999 | Fauquex et al. | |
| 6,033,368 A | 3/2000 | Gaston, IV et al. | |
| 6,143,556 A | 11/2000 | Trachtenberg | |
| 6,284,752 B1 | 9/2001 | Abrams et al. | |
| 6,569,688 B2 | 5/2003 | Sivan et al. | |
| 6,645,518 B2 | 11/2003 | Tedeschi et al. | |
| 6,682,732 B1 | 1/2004 | Blake et al. | |
| 6,841,166 B1 | 1/2005 | Zhang et al. | |
| 2002/0115559 A1 | 8/2002 | Batchelor et al. | |
| 2004/0224868 A1 | 11/2004 | Meyerhoff et al. | |

FOREIGN PATENT DOCUMENTS

| | | |
|---|---|---|
| WO | WO 95/04078 | 2/1995 |
| WO | WO 99/09912 | 3/1999 |
| WO | WO 00/02501 | 1/2000 |
| WO | WO 00/11965 | 3/2000 |
| WO | WO 00/12112 | 3/2000 |
| WO | WO 00/27887 | 5/2000 |
| WO | WO 02/056904 | 7/2002 |
| WO | WO 2005/011575 | 2/2005 |

OTHER PUBLICATIONS

International Search Report for S.N. PCT/US2004/034613 dated May 18, 2005 (18 pages).
European Search Report for S.N. EP 02 70 75 32 dated Mar. 15, 2005 (5 pages).
Supplemental European Search Report for S.N. EP 02 70 75 32.4 dated Jun. 23, 2005 (8 pages).
Annich, G.M. et al., "Reduced platelet activation and thrombosis in extracorporeal circuits coated with nitric oxide release polymers," Crit. Care. Med. 2000 v. 28 915-920 (6 pages).
Batchelor, M.M. et al., "More Lipophilic Dialkyldiamine-Based Diazeniumdiolates: Synthesis, Characterization, and Application in Preparing Thromboresistant Nitric Oxide Release Polymeric Coatings," J Med Chem (2003), 46: pp. 5153-5161.
Batchelor M.M. et al., "Preparation and characterization of nitric oxide releasing polyurethanes for implantable sensor applications," Sixth World Biomaterials Congress, Kanuela, HI, May 17, 2000, Abstract only (1 page).
Batchelor, M.M. et al., "More biocompatible polyurethanes via nitric oxide release," Abstracts of Papers of the American Chemical Society 222: 405-POLY Part 2, Aug. 2001, Abstract only, (2 pages).
Batchelor, M.M. et al., "More biocompatible polymers via nitric oxide release," University of Washington Engineered Biomaterials Conference, Seattle, WA, Aug. 19, 2001 (1 page).
Batchelor, M.M. et al., "Synthesis of nitric oxide-releasing polyurethane," Proc Am Chem Soc Div PMSE 2001; 84: 594, Abstract only (2 pages).
Batchelor, M.M. et al., "Analytical characterization of novel nitric oxide releasing polymeric films containing diazeniumdiolates," Pittsburg Conference New Orleans, LA, Abstract 1217, Mar. 16, 2000, Abstract only (1 page).
Cha, W. et al., "Direct Detection of S-Nitrosothiols Using Planar Amperometric Nitric Oxide Sensor Modified with Polymeric Films Containing Catalytic Copper Species," Anal Chem (2005), 77: pp. 3516-3524.
Cha, W. et al., "S-Nitrosothiol Detection via Ampometric Nitric Oxide Sensor Modified with Polymer film Containing Catalytic Lipophilic Cu(II)-Complex," The Pittsburgh Conference on Analytical Chemistry and Applied Spectroscopy, Orlando, FL (2005), Abstract only, (2 pages).
Chandra, S. et al., "Synthesis and spectral studies on copper (II) complexes of two twelve-membered and tetradentate macrocyclic ligands," Indian Journal of Chemistry, (Dec. 1998), 37A: pp. 1074-1078.

(Continued)

Primary Examiner — David Naff
(74) Attorney, Agent, or Firm — Dierker & Associates, P.C.

(57) ABSTRACT

A device for detecting nitrosothiol content in a solution includes at least two electrodes disposed in a housing, wherein one of the at least two electrodes is a working electrode having a platinized tip and the other of the at least two electrodes is a counter electrode. A filter membrane is disposed at an end of the housing and is configured to come in contact with the solution. The filter membrane and at least a portion of the working electrode have a material coated thereon. The material includes a polymer and a source of copper dispersed within the material. The material and the platinized tip are configured to come into contact with the solution containing nitrosothiols to convert the nitrosothiols to nitric oxide in order to detect the nitrosothiol content.

4 Claims, 7 Drawing Sheets

OTHER PUBLICATIONS

Doel, J. J. et al., "Reduction of Organic Nitrates to Nitric Oxide Catalyzed by Xanthine Oxidase: Possible Role in Metabolism of Nitrovasodilators," Biochemical and Biophysical Research Communications., vol. 270, No. 3, pp. 880-885 (Apr. 2000).

Espadas-Torre, C. et al., "Thromboresistant Chemical Sensors Using Combined Nitric Oxide Release/Ion Sensing Polymeric Films," J Am Chem Soc (1997), 119: pp. 2321-2322.

Fleser, P.S, et al., "Nitric oxide-releasing biopolymers inhibit thrombus formation in a sheep model of arteriovenous bridge grafts," J Vasc Surg 2004, 40: pp. 803-811.

Frost, M.C. et al., "In Vivo biocompatibility and analytical performance of intravascular Clarke-style amperometric oxygen sensors fabricated with NO-releasing polymers," Pittsburgh Conference on Analytical Chemistry and Applied Spectroscopy, Orlando, FL, Mar. 13, 2003, Abstract only (1 page).

Frost, M.C. et al., "Improved in vivo biocompatibility and analytical performance of implanted electrochemical oxygen sensors via nitric oxide release," NAMS, Lexington, KY, May 16, 2001, Abstract only (2 pages).

Frost, M.C. et al., "Improved in vivo biocompatibility and analytical performance of implanted electrochemical oxygen sensors via nitric oxide release," European Society for Biomaterials Meeting, London, England, Sep. 13, 2001, Abstract only (2 pages).

Frost, M.C. et al., "Improved in vivo biocompatibility and analytical performance of implanted electrochemical oxygen sensors via nitric oxide release," Gordon Research Conference on Bioanalytical Sensors, Ventura, CA Mar. 12, 2002, Abstract only (1 page).

Frost, M.C. et al., "Synthesis and characterization of S-nitrosothiol derivatized fumed silica for use as nitric oxide releasing polymer fillers," Society for Biomaterials Meeting, Tampa, FL, Apr. 25, 2002, Abstract only (1 page).

Frost, M.C. et al., Controlled Photoinitiated Release of Nitric Oxide from Polymer Films Containing S-Nitroso-N-acetyl-DL-penicillamine Derivatized Fumed Silica Filler, J Am Chem Soc (2004), 126: pp. 1348-1349.

Frost, M.C. et al., "Improved In Vivo biocompatibility and Analytical Performance of Implanted Electrochemical Oxygen Sensors via Nitric Oxide Release," Society for Biomaterials Meeting, Reno, NV, May 3, 2003, Abstract only (1 page).

Frost, M.C. et al., "Gore-tex vascular grafts with silicone rubbers capable of releasing nitric oxide for sustained times," American Society for Artificial Internal Organs, Washington, DC, Jun. 21, 2003, Abstract only (1 page).

Frost, M.C. et al., "Improved in vivo biocompatibility and analytical performance of implanted electrochemical oxygen sensors via nitric oxide release," Society for Biomaterials Meeting, St. Paul, MN Apr. 27, 2001, Abstract only (1 page).

Frost, M.C. et al., "Synthesis and characterization of S-nitrosothiol derivatized fumed silica used as nitric oxide releasing polymer fillers," American Chemical Society National Meeting, San Diego, CA Apr. 2, 2001, Abstract 345 only (2 pages).

Frost, M.C. et al., "Analytical characterization of S-nitrosothiol derivatized fumed silica," Pittsburgh Conference on Analytical Chemistry and Applied Spectroscopy, New Orleans, LA Mar. 8, 2001, Abstract only (1 page).

Frost, M.C. et al., "Fabrication and In Vivo Evaluation of Nitric Oxide-Releasing Electrochemical Oxygen-Sensing Catheters," Meth Enzymol (2004), 381: pp. 704-715.

Frost, M.C. et al., "Implantable chemical sensors for real-time clinical monitoring: progress and challenges," Curr Opin Chem Biol (2002), 6: pp. 633-641.

Frost, M.C. et al, Polymers incorporating nitric oxide releasing/generating substances for improved biocompatibility of blood-contacting medical devices, Biomaterials (2005), 26: pp. 1685-1693.

Frost, M.C. et al., "Preparation and characterization of implantable sensors with nitric oxide release coatings," Microchemical Journal, 74 (2003) 277-288.

Frost, M.C. et al., "Synthesis, characterization, and controlled nitric oxide release from S-nitrosothiol-derivatized fumed silica polymer filler particles," J Biomed Mater Res A (2005), 72A: pp. 409-419.

Frost, M.C. et al., "In Vivo Biocompatibility and Analytical Performance of Intravascular Amperometric Oxygen Sensors Prepared with Improved Nitric Oxide Releasing Silicone Rubber Coating," Anal Chem (2002), 74: pp. 5942-5947.

Hwang, S.Y. et al., "Covalently attached Cu(II)-complex hydrogel as novel hemocompatible materials," Abstracts of Papers of the American Chemical Society 228: 292-POLY, Part 2 Aug. 22, 2004, 228th National Meeting of the American-Chemical-Society, Philadelphia, PA, Aug. 22-26, 2004, Abstract only (3 pages).

Hwang, S.Y. et al., "Covalently attached Cu(II)-complex hydrogel as novel hemocompatible materials," Abstracts of Papers of the American Chemical Society 228: 292-POLY, Part 2 Aug. 22, 2004, 228th National Meeting of the American-Chemical-Society, Philadelphia, PA, Aug. 22-26, 2004, Amer Chem Soc.

Lee, Y. et al., "Improved Planar Amperometric Nitric Oxide Sensor Based on Platinized Platinum Anode. 1. Experimental Results and Theory When Applied for Monitoring NO Release from Diazeniumdiolate-Doped Polymer Films." Anal Chem (2004); 76: pp. 536-544.

Lee, Y. et al., "Improved Planar Amperometric Nitric Oxide Sensor Based on Platinized Platinum Anode. 2. Direct Real-Time Measurement of NO Generated from Porcine Kidney Slices in the Presence of L-Arginine, L-Arginine Polymers, and Protamine," Anal Chem (2004), 76: pp. 545-551.

Meyerhoff, M.E., "Use of Nitric oxide Releasing/Generating Polymeric Coatings to Enhance the Biocompatibilty of Implanted Chemical Sensors," $229^{th}$ American Chemical Society Meeting, San Diego, CA, Mar. 2005, Analytical 340, Abstract only (1 page).

Meyerhoff, M.E. et al., "Intravascular Chemical Sensors: Can in Situ Nitric Oxide Release Solve Lingering Blood compatibility/Analytical Performance Problems?" The Pittsburgh Conference on Analytical Chemistry and Applied Spectroscopy, New Orleans, LA, Abstract 1188, (2000), Abstract only (1 page).

Meyerhoff, M.E., "Improving the bioanalytical chemistry of in vivo chemical sensors using controlled nitric oxide release," Abstracts of Papers of the American Chemical Society 228: 132-ANYL, Part 1 Aug. 22, 2004, 228th National Meeting of the American-Chemical-Society, Philadelphia, PA, Aug. 22-26, 2004, (1 page).

Meyerhoff, M.E. et al., Enhancing the biocompatibility and in vivo performance of intravascular chemical sensors using nitric oxide release polymers. Abstracts of Papers of the American Chemical Society 218: U165-U165 132-ANYL Part 1, Aug. 22, 1999, Abstract only (2 page).

Mowery, K.A. et al., "More Biocompatible Electrochemical Sensors Using Nitric Oxide Release Polymers," Electroanalysis (1999), 11: pp. 681-686.

Mowery, K.A. et al., "Preparation and characterization of hydrophobic polymeric films that are thromboresistant via nitric oxide release," Biomaterials (2000), 21: pp. 9-21.

Mowery, K.A, et al., "The transport of nitric oxide through various polymeric matrices," Polymer Commun(1999), 40: pp. 6203-6207.

Mowery, K.A. et al., "Thromboresistant Ion-Selective Electrodes Via Nitric Oxide Release Polymeric Membranes," The Pittsburgh Conference on Analytical Chemistry and Applied Spectroscopy, New Orleans, LA (1998), Abstract only (1 page).

Mowery, K.A. et al., "Polymeric diazeniumdiolates for fabricating thromboresistant electrochemical sensors via nitric oxide release," Abstracts of Papers of the American Chemical Society 216: U821-U821 034-PMSE Part 2, Aug. 23, 1998, Abstract only (2 pages).

Mowery, K.A. et al., "More biocompatible electrochemical sensors through the use of combined nitric oxide release ion sensing polymeric films," Abstracts of Papers of the American Chemical Society 213: 339-PMSE Part 2, Apr. 13, 1997, Abstract only (2 pages).

Mowery, K.A. et al., "More Biocompatible electrochemical sensors using nitric oxide release polymers," International Symposium on Electrochemical and Biosensors, Matrafured, Hungary 1998 (2 pages).

Negele, J.C. et al., "Nitric-oxide releasing indwelling oxygen sensors: Thromboresistivity and performance in dogs," Anesthesia and Analgesia 90 (2): U90-U90 S134 Suppl. S, Feb. 2000, Abstract only (1 page).

Oh, B.K. et al., "Spontaneous Catalytic Generation of Nitric Oxide from S-Nitrosothiols at the Surface of Polymeric Films Doped with Lipophilic Copper(II) Complex," J Am Chem Soc (2003), 25: pp. 9552-9553.

Oh, B.K. et al., "Direct Electrochemical Measurement of Nitric Oxide Release Profile from Diazeniumdiolate Doped Polymer Films," Presentation 340, Pittsburg Conference New Orleans, LA, 2000, Abstract only (1 page).

Oh, B.K. et al., "Study of Ion Mediated Reduction of Nitrite to Nitric Oxide (NO) by Ascorbate," Presentation 646, Pittsburg Conference New Orleans, LA, 2001, Abstract only (1 page).

Oh, B.K. et al., "Copper-Complex Mediated Nitrite Reduction to Nitric Oxide (NO) at the Polymer/Solution Interface by L-Ascorbate," Society for Biomaterials Meeting—28$^{th}$ Annual, Tampa, FL, Apr. 25, 2005, Abstract only (1 page).

Oh, B.K. et al., "Catalytic generation of nitric oxide from nitrite at the interface of polymeric films doped with lipophilic Cu(II) complex: a potential route to the preparation of thromboresistant coatings," Biomaterials (2004), 25: pp. 283-293.

Oh, B. K. et al., Biomimetic nitric oxide (NO) generation at interface of polymeric materials doped with lipophilic copper(II)-complex,: Dissertation Abstracts International, vol. 64, No. 9B, p. 4325 (one page) (2003).

Parzuchowski, P.G. et al., "Synthesis and Characterization of Polymethacrylate-Based Nitric Oxide Donors," Am Chem Soc (2002), 124: pp. 12182-12191.

Parzuchowski, P.G. et al., "Synthesis of potentially more blood compatible nitric oxide releasing acrylic copolymers," Abstracts of Papers of the American Chemical Society 221: U298-U298 27-POLY Part 2, Apr. 1, 2001, Abstract only (2 pages).

Reynolds, M.M. et al., "Nitric Oxide Releasing Hydrophobic Polymers: Preparation, Characterization, and Potential Biomedical Applications," Free Rad Biol Med (2004), 37: pp. 926-936.

Reynolds, M.M., "Biomimetic Surfaces for Vascular Devices," 8$^{th}$ UWEB Summer Symposium, Poster Presentation, Seattle, WA, Aug. 25, 2004, Abstract only (1 page).

Roy-Chaudhury, P. et al., "Local nitric oxide delivery systems: Implications for transplant preservation," American Journal of Transplantation 4: 842, Suppl. 8 2004, American Transplant Congress, Boston, MA, May 14-19, 2004, Amer Soc Transplant Surg; Amer Soc Transplant, Abstract only (1 page).

Roy-Chaudhury P. et al., "Local nitric oxide delivery systems for dialysis access grafts," Journal of the American Society of Nephrology 14: 508A-508A, Suppl. S Nov. 2003, 36th Annual Meeting of the American-Society-of-Nephrology, San Diego, California, Nov. 12-17, 2003, Amer Soc Nephrol SA-PO950, Abstract only (1 page).

Saavedra, J.E. et al., "Conversion of a Polysaccharide to Nitric Oxide-Releasing Form. Dual-Mechanism Anticoagulant Activity of Diazeniumdiolated Heparin," Bioorg Med Chem Letters (2000), 10: pp. 751-753.

Schoenfisch et al., "Improving the Thromboresistivity of Chemical Sensors via Nitric Oxide Release: Fabrication and in Vivo Evaluation of NO-Releasing Oxygen-Sensing Catheters," Anal. Chem. (2000) 72: pp. 1119-1126.

Schoenfisch, M.H. et al., "Nitric Oxide Releasing Fluorescence-Based Oxygen Sensing Polymeric Films," Anal Chem (2002), 74: pp. 5937-5941.

Schoenfisch, M.H. et al., "Improving the biocompatibility of intravascular amperometric oxygen sensors via nitric oxide release," Abstracts of Papers of the American Chemical Society 216: U158-U158 062-ANYL Part 1, Aug. 23, 1998, Abstract only (2 pages).

Schoenfisch, M.H. et al. "Thromboresistant Fluorescent Optical Sensors via Nitric Oxide Release," The Pittsburgh Conference on Analytical Chemistry and Applied Spectroscopy, Abstract 728, (1999), Abstract only (1 page).

Wu, Y., "In Situ Generation of Nitric Oxide (NO) at Polymer/Blood Interface: Enhancing the Thromboresistivity of Intravascular chemical Sensors and Other Biomedical Devices," Poster presentation. 8$^{th}$ UWEB Summer Symposium, Seattle, WA, Aug. 25, 2004, Abstract only (1 page).

Ye, Q. et al., "Surface Morpohology of Thrombsoresistant Nitric Oxide Release Polymeric Membranes," The Pittsburgh Conference on Analytical Chemistry and Applied Spectroscopy, New Orleans, LA, Abstract 334, (2000), Abstract only (1 page).

Zhang, H. et al., "Nitric oxide releasing silicone rubbers with improved blood compatibility: preparation, characterization, and in vivo evaluations," Biomaterials (2002), 23: pp. 1485-1494.

Zhang, H. et al., "Polymer Films or Coatings Embedded with Nitric Oxide Releasing Fumed Silica Particles," The 222$^{nd}$ American Chemical Society National Meeting, Chicago, IL, United States, Aug. 26-30, 2001, Abstract only (2 pages).

Zhang, H. et al., "Novel Silicone Materials with Improved Thromboresistance via Nitric Oxide Release," The 221$^{st}$ American Chemical Society National Meeting, San Diego, CA, United States, Apr. 1-5, 2001, Abstract only (2 pages).

Zhang, H. et al., "Potentially More Blood Compatible Polymers Using Nitric Oxide Release Fumed Silica as Fillers," The 220$^{th}$ American Chemical Society National Meeting, Washington DC, United States, Aug. 20-24, 2000, Abstract only (3 pages).

Zhang, H. et al., "More Blood Compatible Silicone Rubbers via Nitric Oxide Release," The 6$^{th}$ World Biomaterials Congress, Hawaii, United States, May 15-20, 2000, Abstract only (2 pages).

Zhang, H. et al., "Synthesis of Nitric Oxide Releasing Silicone Rubbers for Biomedical Applications," The 218$^{th}$ American Chemical Society National Meeting, New Orleans, LA, United States, Aug. 22-26, 1999, with Abstract (4 pages).

Zhang, H. et al., "Nitric Oxide-Releasing Fumed Silica Particles: Synthesis, Characterization, and Biomedical Application," J Am Chem Soc (2003), 125: pp. 5015-5024.

Zhou, Z. et al., "Combining Nitric Oxide Release with Surface Bound Heparin: A Potentially More Thromboresistant Polymeric Coating for Medical Devices," The University of Washington Engineered Biomaterials 8$^{th}$ Summer Symposium, University of Washington, Seattle, WA, USA, Aug. 25-27, 2004, Abstract only (1 page).

Zhou Z.R. et al., "Design, synthesis and characterization of nitric oxide releasing acrylic copolymers with potentially improved blood compatibility," Abstracts of Papers of the American Chemical Society 226: 542-POLY, Part 2 Sep. 2003, 226th National Meeting of the American-Chemical-Society, New York, New York, Sep. 7-11, 2003, Amer Chem Soc 19, Abstract only (2 pages).

* cited by examiner

SCHEMATIC OF SURFACE NO GENERATION VIA
NITRITE REDUCTASE ACTIVITY AND
POLYMER LOADED WITH NITRITE SALT

R= TRIDODECYLMETHYLAMMONIUM

NO RELEASING PROFILE FROM NITRITE ION-PAIR
DOPED POLYMER FILMS IN SHEEP BLOOD

*DISTANCE BETWEEN POLYMER SURFACE
AND SENSOR IS 10 μm

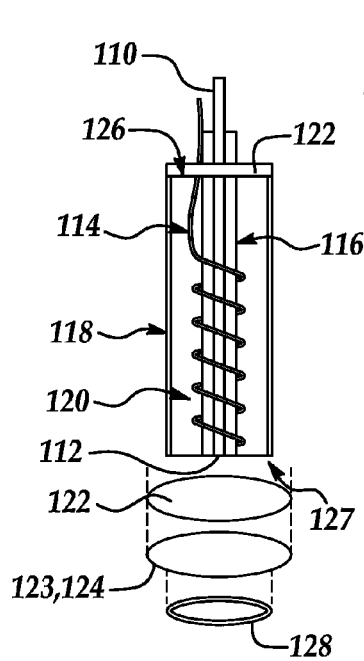
*Figure 9A*
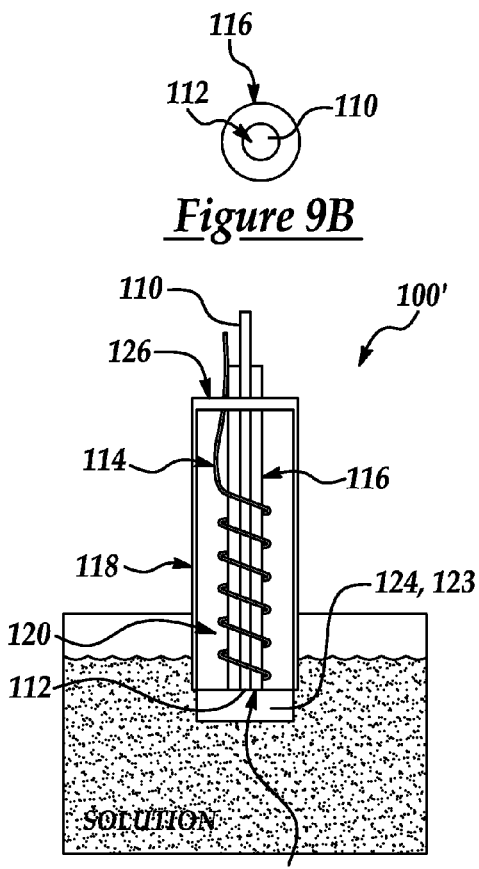
*Figure 9B*
*Figure 9C*
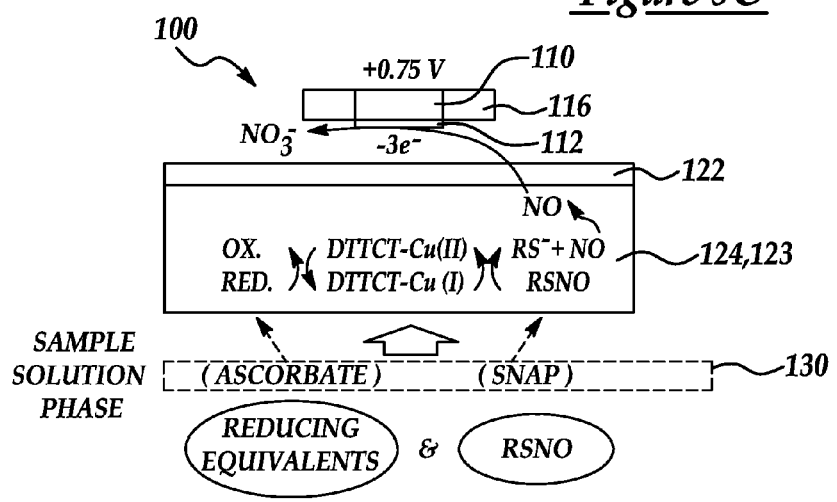
*Figure 10*

DEVICE FOR DETECTING NITROSOTHIOL CONTENT IN SOLUTION

CROSS REFERENCE TO RELATED APPLICATIONS

This application is a divisional of U.S. patent application Ser. No. 11/944,034 filed Nov. 21, 2007 now U.S. Pat. No. 8,034,384, which itself is a continuation of U.S. patent application Ser. No. 10/794,878 filed Mar. 5, 2004, now U.S. Pat. No. 7,335,383, which itself is a continuation-in-part of U.S. Ser. No. 10/052,239 filed on Jan. 16, 2002, now U.S. Pat. No. 7,128,904, which itself claims the benefit of U.S. Provisional Patent application Ser. No. 60/262,014 filed on Jan. 16, 2001. Each of the above-identified applications is incorporated by reference herein in its entirety.

STATEMENT REGARDING FEDERALLY SPONSORED RESEARCH OR DEVELOPMENT

This invention was made in the course of research partially supported by a grant from the National Institutes of Health, Grant Number GM 56991. The U.S. government has certain rights in the invention.

BACKGROUND

This invention relates generally to the generation of nitric oxide in situ and to nitric oxide sensors, and more particularly to biocompatible materials having surfaces that are capable of generation of nitric oxide in situ when contacted with nitrite, nitrate or nitrosothiols in blood, and to a reproducible nitric oxide sensor.

Although medical devices such as extracorporeal circuits and hemodialysis tubes are widely used in clinical settings, the polymers typically used to fabricate such devices (PVC, polyurethane, silicone rubber, etc.) are still subject to platelet aggregation and adhesion onto the surface of these materials. Thus, patients are often given anti-clotting agents (i.e., heparin) in order to reduce thrombosis on the surface of these devices. Similarly, implanted devices made of stainless steel or other alloys, or even carbon, can cause thrombus formation when in direct contact with blood. There is, therefore, a need for materials that more closely simulate the antithrombogenic properties of the endothelial cells that line blood vessels in order to obviate the need to administer anticoagulants.

Nitric oxide (NO) is an important intracellular and intercellular messenger molecule that plays an important physiological role in anti-platelet aggregation and anti-platelet activation, vascular relaxation, neurotransmission, and immune response. It has been proposed that synthetic materials that release low levels of NO would, therefore, more closely simulate the natural activity of endothelial cells, and therefore, would have improved biocompatibility.

Several classes of NO-releasing materials are currently under investigation worldwide. These include NO donors (i.e., diazeniumdiolates, nitrosothiols) that may be relatively complicated to synthesize and may in some instances require stringent storage conditions.

Currently, NO generation is determined by water uptake (such as in the case of diazeniumdiolates) or the intensity of light (as with iron nitrosyls). However, blood already contains a host of species that are derived from, or are physiologically-generated in vivo that may be reduced to NO. These species include nitrites, nitrates, and a host of nitrosothiols (e.g., nitrosoglutathione, nitroso albumin, etc.). The presence of these species raises the possibility of recycling these species back to nitric oxide.

S-nitrosothiols (RSNO) are believed to take part in the storage and transportation of NO in biological systems. While RSNOs are generally stable in physiological conditions, they may, in some instances, be sensitive to photolytic breakdown and catalytic decomposition in the presence of transition metals to produce the free thiol and NO. Modification of the membrane design of NO sensors may be used to fabricate a nitrosothiol sensor and thus detect the presence of nitrosothiols in fluids.

SUMMARY

A device for detecting nitrosothiol content in a solution includes at least two electrodes disposed in a housing, wherein one of the at least two electrodes is a working electrode having a platinized tip and the other of the at least two electrodes is a counter electrode. A filter membrane is disposed at an end of the housing and is configured to come in contact with the solution. The filter membrane and at least a portion of the working electrode have a material coated thereon. The material includes a polymer and a source of copper dispersed within the material. The material and the platinized tip are configured to come into contact with the solution containing nitrosothiols to convert the nitrosothiols to nitric oxide in order to detect the nitrosothiol content.

BRIEF DESCRIPTION OF THE DRAWINGS

Features and advantages of embodiment(s) of the present disclosure will become apparent by reference to the following detailed description and drawings, in which:

FIG. 9A is an exploded, partially schematic side view of an embodiment of a nitrosothiol sensor of the present disclosure;

FIG. 9B is an enlarged bottom view of an embodiment of a glass capillary and working electrode;

FIG. 9C is a partially schematic side view of another embodiment of a nitrosothiol sensor of the present disclosure;

FIG. 10 is a schematic representation of the detection of nitrosothiols using an embodiment of the nitrosothiol sensor of the present disclosure;

DETAILED DESCRIPTION OF THE EMBODIMENTS

Figure 1:
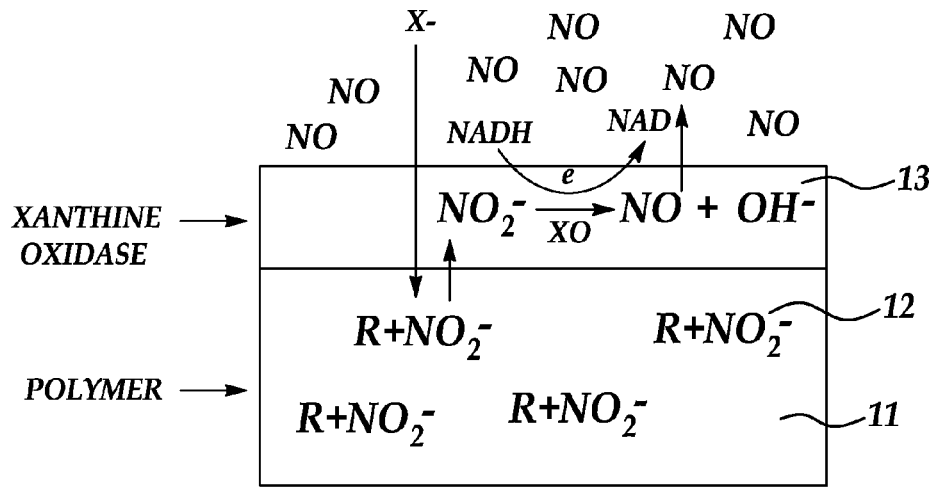
FIG. 1 is a schematic of illustration of NO generation in solution via nitrite reductase activity from the catalytic surface of in a polymer loaded with nitrite salt.

An embodiment of the present disclosure provides a novel, reproducible nitric oxide sensor for the detection of the S-nitrosothiols. In an embodiment, the sensor is coated with a material having a catalytic or consumptive/reactive copper ion complex therein. The sensor may advantageously be used to take numerous measurements of the nitrosothiol content in a sample over several days.

A further embodiment of the present disclosure provides a novel approach for enhancing the biocompatibility of materials of the type suitable for implantation in a human or animal body and/or for prolonged contact with the body or blood. In accordance with a broad aspect of the disclosure, materials have been developed to have reactive agents that are capable of generating, at the materials' surface/blood interface, physiologically significant amounts of NO when in contact with blood. A reactive agent, having nitrite reductase and/or nitrite reductase-like activity, nitrate reductase activity, or nitrosothiol reductase activity, may be immobilized, adsorbed, adhered, or otherwise made available at a surface of the material. Still further, the reactive agent may be covalently attached to a polymer backbone within the material.

As used herein, the term "material," when referring to the material that is provided with the reactive agents, may be any material that may be suitable for contact with the body and/or body fluids, particularly blood, of a living being, e.g., is physiologically acceptable and non-toxic. In some embodiments, the material should be suitable for long-term contact, or in-dwelling uses. Non-limitative examples of such materials include polymers, metals and alloys thereof, and carbon (graphite).

Many polymeric materials are suitable for the practice of the disclosure, and the following illustrative list of polymers that have been used for biomedical applications is not intended to be limiting in any manner. Examples include synthetic polymers such as polyurethanes, polydimethylsiloxane, ethylene vinyl acetate, nylons, polyacrylics, polymethyl methacrylate, polyamides, polycarbonates, polyesters, polyethylenes, polypropylenes, polystyrenes, poly(vinyl chloride) (PVC), polytetrafluoroethylene (PTFE) and cellulose acetate.

In an embodiment, a material includes a hydrophobic polymer, such as poly(vinyl chloride), polyurethane, and silicone rubber, and a layer of a reactive agent having nitrite reductase activity, nitrite reductase-like activity, nitrate reductase activity or nitrosothiol reductase activity attached to a surface of the hydrophobic polymer. The attachment may be by adsorption, covalent bonding, and the like. In an embodiment, the polymer may include lipophilic salts of nitrite/nitrate or nitrosothiols within its matrix to create a reservoir of nitrite/nitrate or nitrosothiol that can continuously leak to the catalytic surface.

In embodiments where the material is a polymer, the NO-releasing polymer may be formed, cast, or otherwise shaped to form a monolithic device, such as implantable devices such as drug depot or in-dwelling devices, catheters, extracorporeal tubing sets (including kidney dialysis or open-heart surgery heart-lung machines), and/or the like. Other examples of such devices include, but are not limited to medical devices such as arterial stents, guide wires, bone anchors, bone screws, protective platings, hip implants, joint implants, spine appliances, electrical leads, biosensors, vascular grafts, heart valves, extracorporeal circuits, and probes. In an alternate embodiment, the material may also be applied as a film on another substrate that may be a polymer, or another surface, such as the surface of a metal device. Suitable metals for such devices include, but are not limited to stainless steel, nickel, titanium, aluminum, copper, gold, silver, platinum and/or combinations thereof.

Further, the material may be a metal substrate. In an embodiment, the metal material may have a reactive agent covalently attached to its surface. It is to be understood that in this embodiment, and other embodiments discussed herein, the reactive agent may be a biomimetic catalytic or consumptive/reactive agent. As used herein the term "biomimetic agent" refers to a species possessing nitrite reductase-like activity, or the ability to reduce nitrosothiols which converts endogenous or exogenous nitrite, nitrate and/or nitrosothiols to NO when in contact with blood.

Illustratively, the biomimetic catalytic agent may be a metal ion ligand complex wherein the metal ion is capable of reducing one or more of nitrate, nitrite, nitrosothiols, and other blood species to nitric oxide. In an embodiment, the metal ion ligand complex is a Cu(II) complex. Neutral carrier type ligands that have high metal binding affinity, particularly for copper, and, preferably, planar square-type geometry that provides a minimum amount of steric hindrance to the approach of the electron source (e.g., ascorbate or NADH) to the center metal of the complex so that the copper ion can easily be reduced from Cu(II) to Cu(I), are suitable for the practice of the disclosure. Non-limitative examples include nitrogen or sulfur donating compounds, such as $N_x$-donor macrocyclic ligands (x=2, 4, 5, 6, 8) such as cyclen, cyclam and their derivatives, and crown ethers and $S_x$-donor macrocyle-type ligands (x=2, 4, 5, 6, 8).

Attachment of the metal ion ligand to the metal surface may be accomplished by any suitable means known to a person of ordinary skill in the art. One such technique involves silanizing the surface of the metal to provide reactive sites to bind the ligand.

In specific illustrative embodiments, the biomimetic catalytic agent is a Cu(II) metal ion ligand complex selected from the group consisting of dibenzo[e,k]-2,3,8,9-tetraphenyl-1,4,7,10-tetraaza-cyclododeca-1,3,7,9-tetraene; dibenzo[e,k]-2,3,8,9-tetramethyl-1,4,7,10-tetraaza-cyclododeca-1,3,7,9-tetraene; dibenzo[e,k]-2,3,8,9-tetraethyl-1,4,7,10-tetraaza-cyclododeca-1,3,7,9-tetraene; and dibenzo[e,k]-2,3,8,9-tetraphenyl-1,4,7,10-tetraaza-cyclodeca-1,3,7,9-tetraene.

In other embodiments, the reactive agents are biocatalysts, such as enzymes, having nitrate reductase activity, nitrite reductase activity, nitrite reductase-like activity, and/or nitrosothiol reductase activity. Illustratively, nitrite reductases, nitrate reductases, enzymes having nitrosothiol reducing ability, xanthine oxidase, and/or combinations thereof may be selected. Due to the ease of procuring xanthine oxidase commercially (e.g., Sigma, St. Louis, Mo.), xanthine oxidase may be used in an embodiment. Other potentially useful immobilized biocatalysts may include nitrite reductases and nitrate reductases from plants or bacteria.

Still further, the reactive agents may be metal complexes (hydrogels) that are covalently attached to the polymer backbone of the material.

In an alternate embodiment, the reactive agent may be a source of metals and/or metal ions that either converts the nitrates, nitrites and/or nitrosothiols, or generates a species capable of converting nitrates, nitrites and/or nitrosothiols to NO. In one embodiment, copper, copper (I) or copper (II) containing materials may be exposed to endogenous or exogenous sources of nitrates, nitrites, or nitrosothiols with appropriate reducing agents to generate the active metal (I) species for the generation of NO at the surface of the material. It is to be understood that the sources of nitrates, nitrites, nitrosothiols and reducing agents may be from the blood, the polymer matrix, the metal substrate, and/or may be injected intravenously. The metal/metal ion source degrades (via corrosion) or leaches onto the surface of the material to yield the required and/or desired catalytic/reactive species that is capable of converting the nitrates, nitrites and/or nitrosothiols to NO. Other non-limiting examples of metal/metal ion sources include calcium, magnesium, cobalt, manganese, iron, molybdenum, tungsten, vanadium, aluminum, chromium, zinc, nickel, platinum, tin, ions thereof, and/or mixtures thereof. Some non-limitative examples of a metal ion source are copper (II) phosphate and various copper salts.

In certain embodiments, an exogenous source of nitrites, nitrates or nitrosothiols is provided in the material to form a reservoir of nitrites, nitrates or nitrosothiols that can continuously leak to the surface of the material. In these embodiments, the exogenous source (a non-limitative example of which includes lipophilic salts of nitrites, nitrates or nitrosothiols) is dispersed within the material. In some embodiments, the material containing the exogenous source of nitrites, nitrates or nitrosothiols is applied to a device as a coating. Some non-limitative examples of nitrites, nitrates or nitrosothiols, include, without limitation, quaternary ammonium salts, such as tridodecylmethylammonium nitrite ($TDMA^+NO_2^-/NO_3^-$); trimethyl phenyl ammonium; dimethyl dioctadecyl ammonium; etc. In addition to quaternary ammonium salts, quaternary phosphonium salts or quaternary arsonium salts may be used in the practice of embodiments of the disclosure.

Methods of making the disclosure include swelling a polymer, such as a polyvinyl chloride (PVC) or silicone, or a polymer-coated device in the presence of an organic solvent containing an appropriate copper (I) or copper (II) containing moiety or the nitrite/nitrate salt to form a copper(I), copper (II) or a nitrite/nitrate salt-containing polymer. The copper(I), copper(II) or nitrite/nitrate salt-containing polymer may then be coated with a layer of immobilized enzyme, illustratively a nitrite reductase enzyme, such as xanthine oxidase. Many techniques are available for immobilizing enzymes. For example, see, Hasselberger, "Uses of Enzymes and Immobilized Enzymes, Nellson-Hall," Chicago (1978) or Guilbault, "Analytical Uses of Immobilized Enzymes," Marcel Dekker, New York (1984). Alternately, the copper(I), copper(II) or nitrite/nitrate salt-containing polymer-coated device may then be dried to return the device to its functional form.

In another embodiment of the inventive method, the biomimetic generation of NO may be further achieved by immobilizing metal-ion ligand complexes, on the surface of the material, or by dispersing these ligands within the material, which, as previously discussed, may be a polymer. In some embodiments, additional lipophilic nitrite/nitrate salts, or nitrosothiols, are added to an underlying polymer matrix material or provided as a coating on the material, or as an additional layer.

In other embodiments, the reactive agent may be added during the processing stage when the desired end product (e.g. device) is molded or cast from the native polymer material. In still other embodiments, the surface of the device that will be exposed to blood, for example, the outside surface of a catheter or the inner surface of tubing of the type used in extracorporeal circuits, or the surface of metal stents, may be coated, either by dip-coating or by another method with the material containing the reactive agent capable of reducing nitrate, nitrite or nitrosothiols to NO.

In an alternate embodiment, the reactive agents (including, but not limited to metal sources, metal ion sources, biocatalysts or biomimetic catalytic or consumptive/reactive agents, and/or the like) may also be covalently tethered to the surface of the material. It is to be understood that covalent macromolecules having a copper containing moiety may be covalently attached to a polymer backbone. One non-limiting example includes a copper cylan complex bound to a polyhydroxyethylmethyloxylate matrix. It is to be understood that such copper complexes may be attached to other polymers, including, but not limited to at least one of polyurethanes and poly(vinyl chlorides).

FIG. 1 illustrates a specific embodiment of the material of the present disclosure. Mammalian xanthine oxidase (XO) is used as a surface catalyst for nitrite reduction to NO. In the presence of nicotinamide adenine dinucleotide (NADH), or other reducing equivalents in blood, the surface catalyst will generate NO as the nitrite ions leak from within the material into this surface layer via exchange for chloride and bicarbonate within the blood. Referring to FIG. 1, a polymer matrix 11 that has been loaded with a lipophilic nitrite/nitrate salt of tridodecylmethylammonium 12 ($TDMA^+NO_2^-$) that provides a source of nitrite ions ($NO_2^-$). A coating 13 of xanthine oxidase (XO) is located at the surface of the polymer matrix 11.

Preliminary feasibility studies have been carried out to demonstrate the basic concept of this disclosure. Using xanthine oxidase as a model enzyme for nitrite reductase activity. PVC polymer films were doped with $TDMA^+NO_2^-$ and then coated with a layer of immobilized XO.

Illustratively, the PVC polymeric film, or membrane, was prepared by a cocktail solution casting method as described, for example, in Mathison et al., Anal. Chem., Vol. 71, pages 4614-4621 (1999) or any of the patents referenced herein. The cocktail solution was prepared by dissolving the appropriate amounts of membrane components (polymer, plasticizers and, in some cases, an ion-exchanger) into a solvent, illustratively tetrahydrofuran (THF). The membranes were cast in a mold to a final thickness of about 150 μm.

The polymer film was then coated with immobilized XO prepared by crosslinking XO with bovine serum albumin (BSA) in the presence of glutaraldehyde. The cross-linked product forms a hydrogel that is dip-coated on the PVC polymer substrate.

An electrochemical sensor was used to probe the surface concentrations of NO generated when the coated film were placed into a buffered solution containing NADH at physiological pH. Significant levels of NO were generated at the surface of the film under these conditions. The generation of NO near the surface of the polymer film continued for several hours as the nitrite in the film was exchanged for anions in the buffer phase.

In this particular embodiment, the electrochemical NO sensor used was similar in style to conventional Clark type oxygen sensor. Glass coated Platinum (Pt) wire served as the anode and Ag/AgCl wire (0.25 mm dia.) was used as the cathode. The internal filling solution was composed of 0.3 mM HCl and 30 mM NaCl, pH 3.5. An outer gas permeable membrane (Goretex, polytetrafluoroethylene with 50% porosity and 0.2 µm pore size) was placed between the internal filling solution and sample solution. Amperometric NO measurements were performed by applying a potential of 0.9 V.

Figure 2:
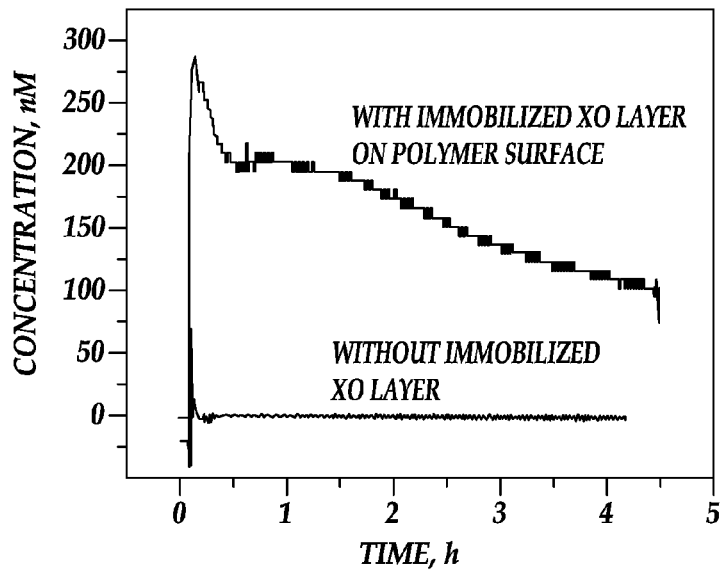
FIG. 2 is a graphical representation of the NO-release profile from nitrite ion-pair doped polymer films having immobilized XO on the surface in the presence of sheep blood.

FIG. 2 graphically illustrates that, when a similar film coated with XO was exposed to whole sheep blood, without adding any reducing equivalents in the form of NADH, measurable levels of NO were generated at the surface of the film as detected by the aforementioned electrochemical NO sensor. This data suggests that there is adequate endogenous reducing equivalent species in blood to serve as the source of electrons for the biocatalytic reaction at the surface of a polymer prepared in accordance with the present disclosure.

In another illustrative embodiment, biomimetic catalysts and/or reactants, such as Cu(II)-ligand complexes, for example, dibenzo[e,k]-2,3,8,9-tetraphenyl-1,4,7,10-tetraaza-cyclododeca-1,3,7,9-tetraene, were either incorporated in or tethered to a polymer or other material surface, such as a metal. Examples of this embodiment are shown in FIGS. 3 and 4.

Figure 3:
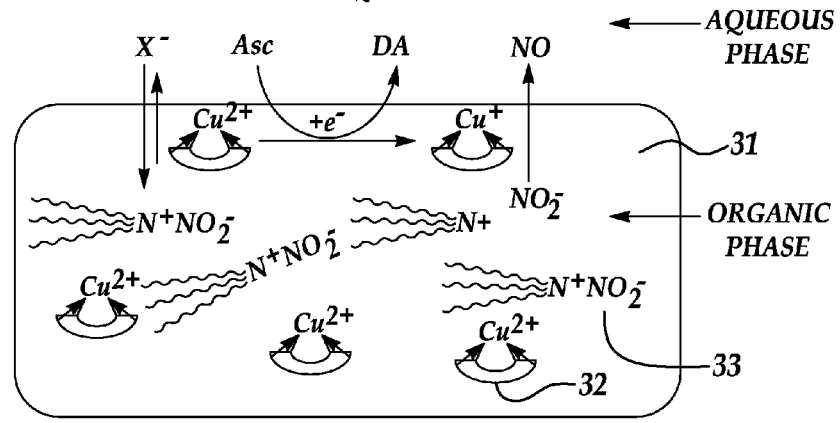
FIG. 3 is a schematic representation of NO generation from a polymer matrix that has been loaded with a nitrate salt and a Cu(II) ligand complex in accordance with the disclosure.

FIG. 3 is a schematic representation of a polymer matrix 31, illustratively PVC, that has been loaded with a lipophilic Cu(II) ligand complex 32 as well as a lipophilic nitrite/nitrate salt of tridodecylmethylammonium 33 (TDMA$^+$NO$_2^-$) that provides a source of nitrite ions (NO$_2^-$) in the polymer. When the polymer is exposed to an aqueous solution containing ascorbate (ASC) or ascorbic acid, the ascorbic acid reduces the Cu(II) in the ligand complex to Cu(I). The Cu(I) in turn reduces nitrites in the film to NO.

Figure 4:
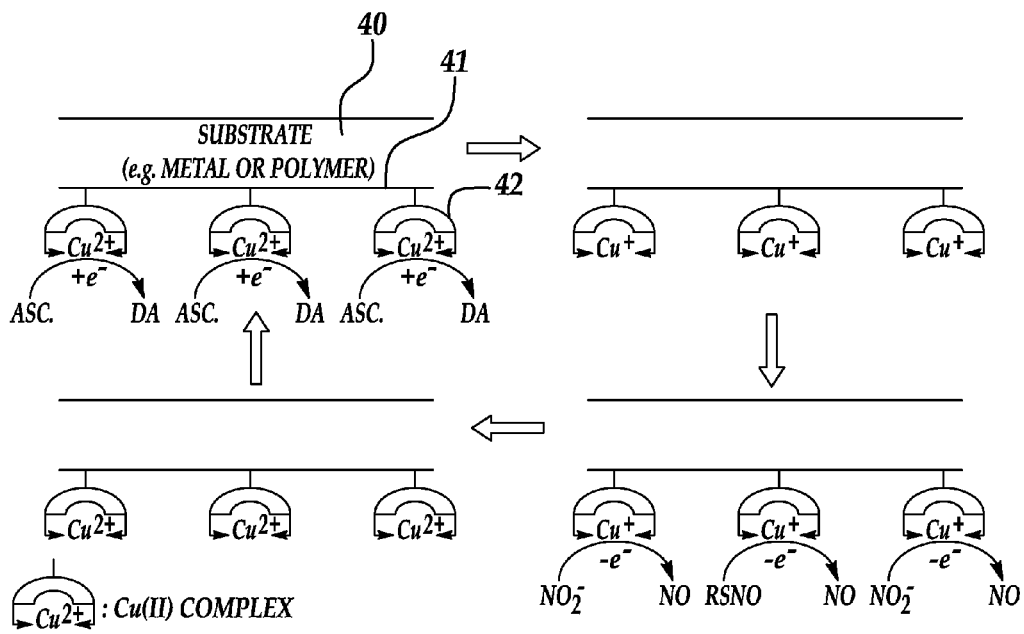
FIG. 4 is a schematic representation of a material, in accordance with the disclosure, wherein a Cu(II) ligand complex is covalently tethered to the surface.

FIG. 4 is a schematic representation of a material 40 that has a catalytic surface 41 created by tethering a Cu(II) ligand complex 42 to the surface. When the catalytic surface is exposed to an aqueous solution, which may be blood, containing ascorbic acid, the ascorbic acid reduces Cu(II) in the ligand to Cu(I). The Cu(I) returns to Cu(II) thereby converting nitrites and nitrosothiols (specifically S-nitrosothiols or RSNOs), for example, in the solution to NO. RSNOs or thionitrites are known to occur endogenously in various biological systems such as human plasma and white blood cells. Some non-limitative examples of RSNOs include the following.

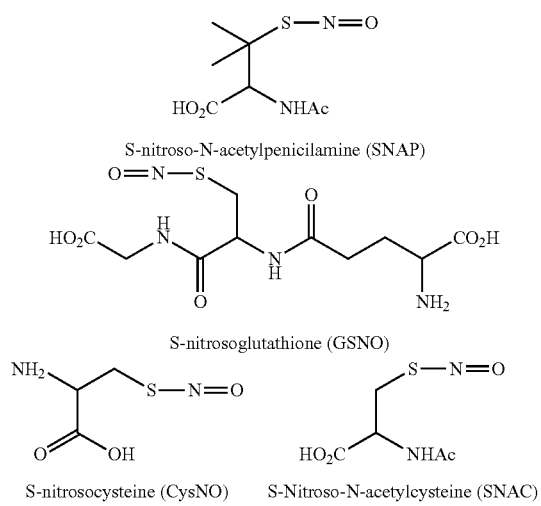

S-nitroso-N-acetylpenicilamine (SNAP)

S-nitrosoglutathione (GSNO)

S-nitrosocysteine (CysNO)    S-Nitroso-N-acetylcysteine (SNAC)

Figure 5:
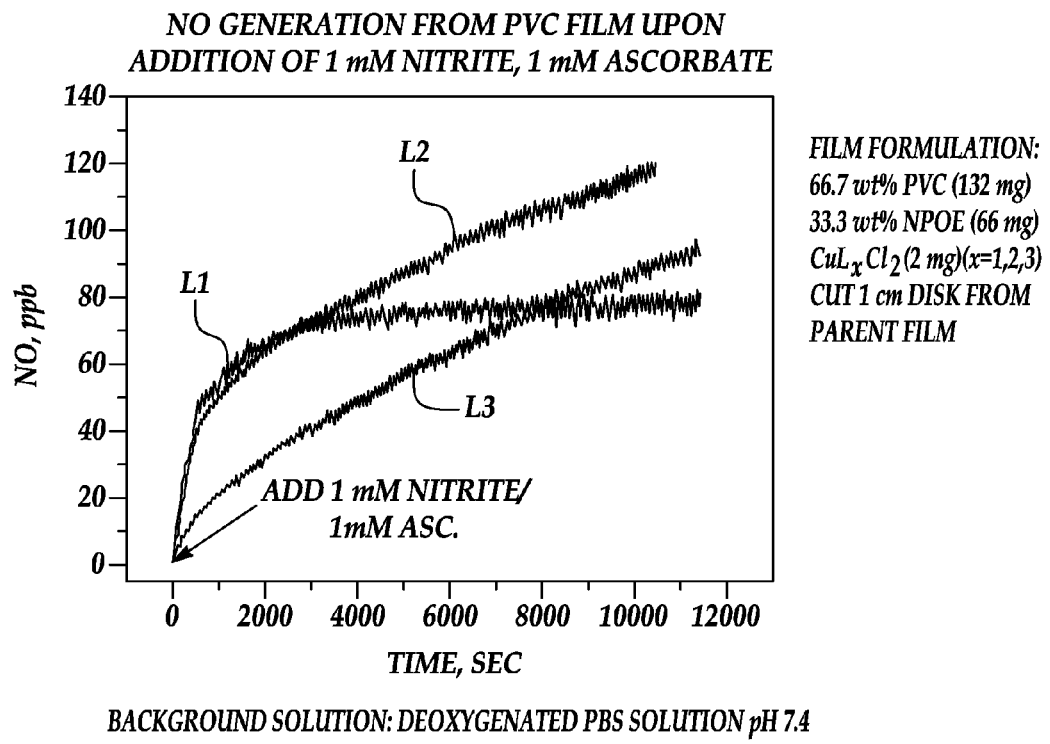
FIG. 5 is a graphical representation of the surface generation of NO from a Cu(II) ligand complex-containing polymer film in a bulk solution containing nitrite and ascorbate.

FIG. 5 is a graphical representation of the surface generation of NO from a Cu(II) ligand complex-containing polymer film in a bulk solution containing nitrite and ascorbate. The data is plotted as NO concentration in parts per billion (ppb) as a function of time in seconds.

Figure 6:
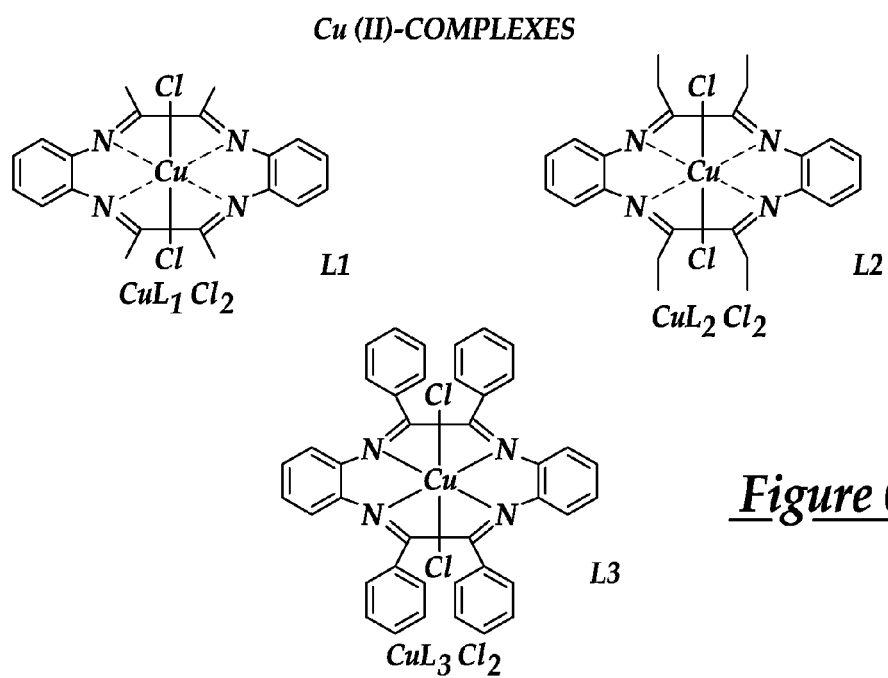
FIG. 6 shows three examples of illustrative metal ligand complexes.

Three films having the following formulation were prepared in accordance with the method set forth above: 66.7 wt % PVC polymer (132 mg); 33.3 wt % plasticizer, illustratively nitrophenyloctyl ether (NPOE; 66 mg), and Cu(II) ligand complex, CuL$_x$C12 (2 mg), L$_x$ being ligands, L1-L3 as shown on FIG. 6. The illustrative metal ligand complexes, specifically Cu(II) ligand complexes, shown on FIG. 6 are Cu(II)-dibenzo[e,k]-2,3,8,9-tetramethyl-1,4,7,10-tetraaza-cyclododeca-1,3,7,9-tetraene (DTTCT-1) labeled L1; Cu(II)-dibenzo[e,k]-2,3,8,9-tetraethyl-1,4,7,10-tetraaza-cyclododeca-1,3,7,9-tetraene (DTTCT-2) labeled L2; and Cu(II)-dibenzo[e,k]-2,3,8,9-tetraphenyl-1,4,7,10-tetraaza-cyclodeca-1,3,7,9-tetraene (DTTCT-3) labeled L3.

Referring back to FIG. 5, traces 61, 62, and 63 being ligands L1-L3, respectively. In this particular experiment, the bulk solution was deoxygenated phosphate buffered saline (PBS) having a pH of 7.4. At time t=0, 1 mM nitrite and 1 nM ascorbate were added to the PBS solution and NO generation was measured with a chemiluminescense detector. The results demonstrate that films in accordance with the present disclosure are capable of NO generation at the interface when the nitrites and ascorbates are in the bulk solution, such as would occur when the films were placed in contact with blood in an in vivo situation.

Figure 7:
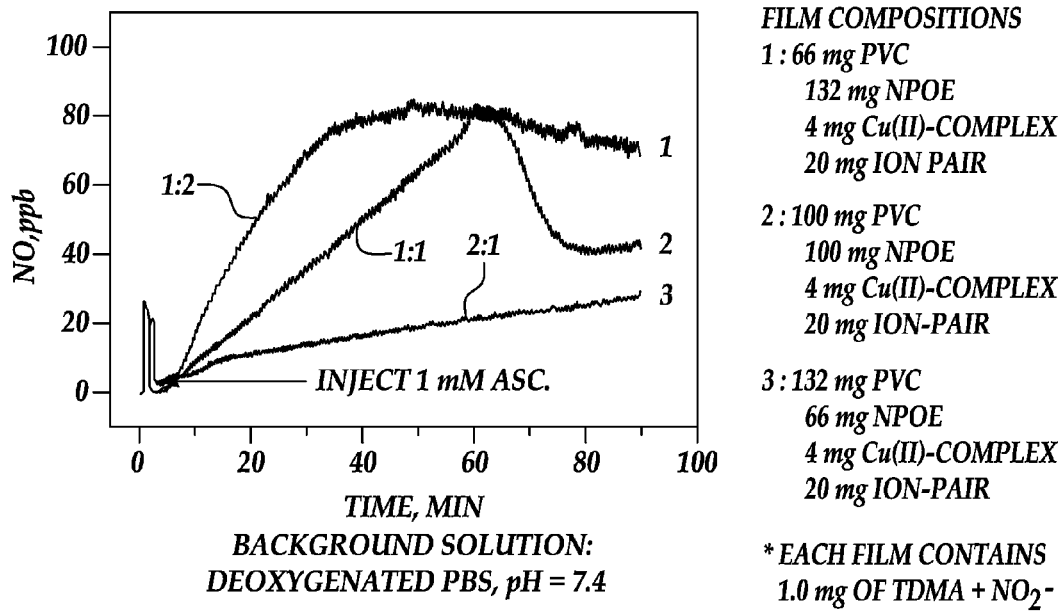
FIG. 7 is a graphical representation of NO generation from a nitrite ion pair/Cu(II) complex, specifically the complex designated L3 in FIG. 6.

FIG. 7 is a graphical representation of NO generation from a nitrite ion pair/Cu(II) complex, specifically the complex designated L2 in FIG. 5, doped into a polymer film. The data is plotted as NO concentration in parts per billion (ppb) as a function of time in minutes following introduction of 1 mM ascorbate into a deoxygenated PBS solution having pH 7.4.

The polymeric film compositions used in this experiment are as follows:

Film 1:
66 mg PVC; 132 mg NPOE; 4 mg Cu(II) complex; and 20 mg ion pair, or TDMA$^+$NO$_2^-$ Film 2:
100 mg PVC; 100 mg NPOE, 4 mg Cu(II) complex; and 20 mg ion pair Film 3:
132 mg PVC; 66 mg NPOE; 4 mg Cu(II) complex; and 20 mg ion pair These results show generation of NO by the polymer film that is particularly good for the highly plasticized embodiments.

Figure 8:
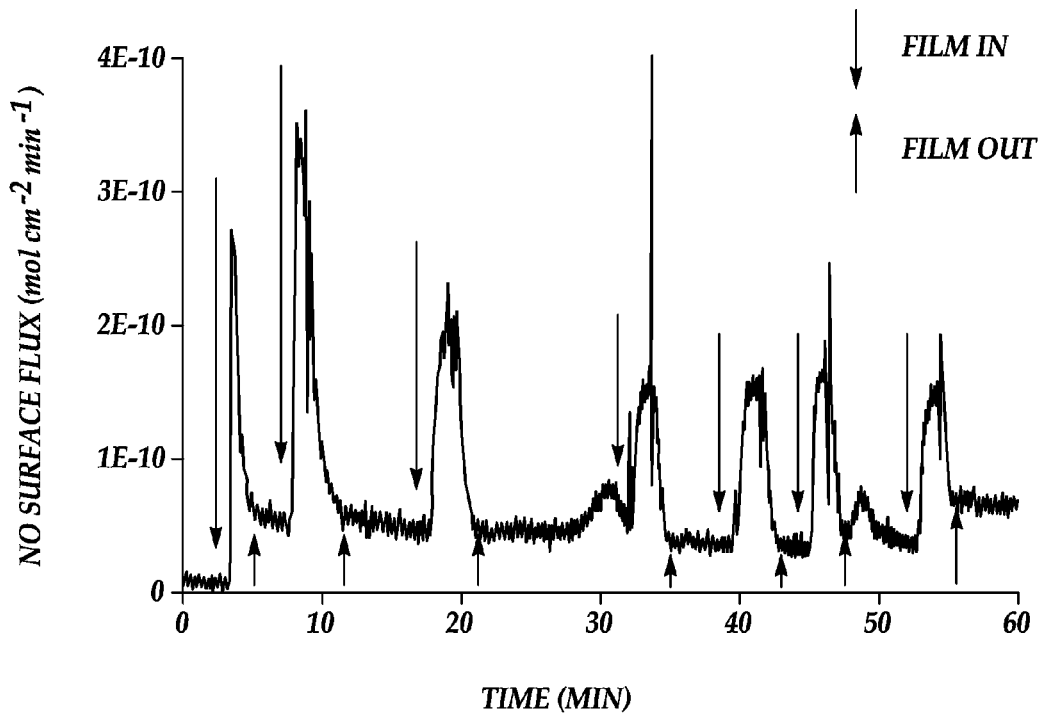
FIG. 8 is a graphical representation of NO surface flux measurements from a plasticized PVC film containing copper metal.

FIG. 8 graphically illustrates the NO surface flux for a plasticized PVC material having copper metal therein. The copper metal acted as a reactive agent to form Cu(I) which in turn converted nitrosothiols to NO under in vitro conditions.

Referring now to FIG. 9A, an embodiment of the present disclosure also includes a reproducible nitrosothiol sensor device 100 that is capable of detecting the amount of nitrosothiol in various solutions, including, but not limited to blood. In an embodiment, the NO sensor device 100 includes a working electrode 110 having a platinized tip 112, a counter electrode 114, a glass capillary 116, a housing 118 having a space 120 therein for an internal filling solution, a membrane 122, and a filter membrane 123 (a non-limitative example of the filter membrane 123 material is PTFE) coated with material 124 (a non-limitative example of material 124 is hydrophilic PU (Tecophilic SP60D-20) containing Cu-DTTCT complex (10% (wt)). Material 124 also coats the working electrode 110. A suitable seal 128, such as an O-ring, may be used. FIG. 9B is an enlarged bottom view of the working electrode 110, the platinized tip 112, and the glass capillary 116.

In an embodiment, the housing 118 is configured to hold the glass capillary 116, the working electrode 110, and the counter electrode 114. It is to be understood that the housing 118 is also configured to have a space 120 therein that may be filled with an internal filling solution (not shown). Still further, the housing 118 has a membrane 122 covering opposed open ends 126, 127. It is to be understood that any suitable material may be used for the housing 118. In an embodiment, the housing 118 is formed from polypropylene.

The membrane 122 is configured to receive the working electrode 110, the counter electrode 114, and the glass capillary 116, as all three elements 110, 114, and 116 extend and/or protrude from upper end 126 of the housing 118. At lower end 127, membrane 122, and filter membrane 123 (and subsequently working electrode 110) come in contact with external solutions/samples 130 (shown in FIG. 10). The membrane 122 may be made of any suitable material, a non-limitative example of which includes polytetrafluoroethylene (PTFE).

It is to be understood that any suitable electrode materials may be used for the working electrode 110 and the counter electrode 114 as long as one acts as an anode and the other acts as a cathode. In an embodiment, the working electrode 110 is a platinum wire and the counter electrode 114 is a silver wire. The counter electrode 114 is in close proximity to, but spaced from the membrane 122.

In an embodiment, the glass capillary 116 is centered within the housing 118 and has a portion protruding through the membrane 122 and out the upper end 126 of the housing 118.

The working electrode 110 is positioned such that the glass capillary 116 substantially surrounds the working electrode 110. It is to be understood that the portion of the working electrode 110 that extends from the end 126 of the housing 118 extends further than that of the glass capillary 116, therefore a portion of the working electrode is not surrounded by the glass capillary 116.

The working electrode 110 (prior to being inserted in the glass capillary 116) may also be substantially coated with material 124 that advantageously assists in obtaining numerous nitrosothiol measurements. It is to be understood that the polished and platinized tip 112 of the working electrode 110 may not be coated with the material 124, while the rest of the working electrode 110 may be coated. The material 124 includes a polymer having a source of copper, which acts as a catalyst or a reducing agent, therein. It is to be understood that any suitable polymer may be selected. Examples of suitable polymers include, but are not limited to hydrophilic polyurethanes, PTFE, poly(vinyl chloride), silicon rubbers and/or mixtures thereof. In an embodiment, a hydrophilic polyurethane is selected due in part to its high water-uptake capability.

It is to be further understood that the source of copper within the material 124 may be an inorganic copper source (such as copper particles and copper compounds/salts (a non-limitative example of which is copper (II) phosphate)) and/or a copper complex (including those illustrated in FIG. 6) and/or mixtures thereof. In an embodiment using copper particles, it is contemplated that the copper particles have an average size of about 3 μm and also have a dendritic structure. One embodiment may incorporate EDTA-Cu complexes, however it is contemplated that EDTA-Cu complexes generally have substantially no effect on RSNO decomposition because EDTA chelating ligands sterically are not able to access RSNOs.

A non-limitative example of the material 124 may be prepared by adding 2 mg of DTTCT (or 2 mg of copper particles) and about 20 mg of polyurethane to about 1 mL of tetrahydrofuran (THF).

Another device 100' for detecting nitrosothiol content in a solution is shown in FIG. 9C. The device 100' includes at least two electrodes 110, 114 disposed in a housing 118 having two opposed ends 126, 127. One of the electrodes 110 is a working electrode having a platinized tip 112. The other electrode 114 is a counter electrode. A glass capillary 116 is supported within the housing 118 and protrudes beyond one of the opposed housing ends 126. A filter membrane 123 is disposed at the other opposed end 127 of the housing and is configured to come in contact with the solution. The filter membrane 123 and at least a portion of the working electrode 110 have a material 124 coated thereon. The material 124 includes a polymer and a source of copper dispersed within the material 124. The material 124 and the platinized tip 112 are configured to come into contact with the solution containing nitrosothiols to convert the nitrosothiols to nitric oxide in order to detect the nitrosothiol content.

For illustrative purposes, FIG. 10 is a schematic representation of the amperometric detection using the nitrosothiol sensor device 100 of the present disclosure. When the nitrosothiol sensor device 100 (specifically the material 124, and the platinized tip 112) contacts a solution/sample 130 (e.g. blood) containing a reducing agent (e.g. RSH/RS or ascorbate) and a nitrosothiol (e.g. RSNO), the Cu(II) reduces to Cu(I). The reduced metal ion (Cu(I)) decomposes RSNOs rapidly in the presence of the reducing agent. The following are the equations representing the reduction of Cu(II) and the formation of NO:

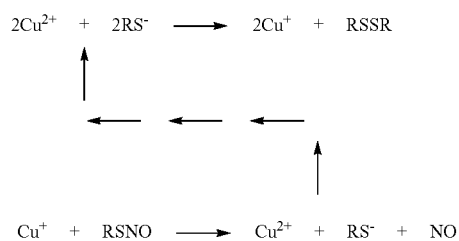

Upon contacting the nitrosothiol sensor device 100 with the sample containing RSNO, the nitrosothiol sensor device 100 detects the released NO, which then allows the user to calculate the amount of RSNO in the sample.

Figure 11:
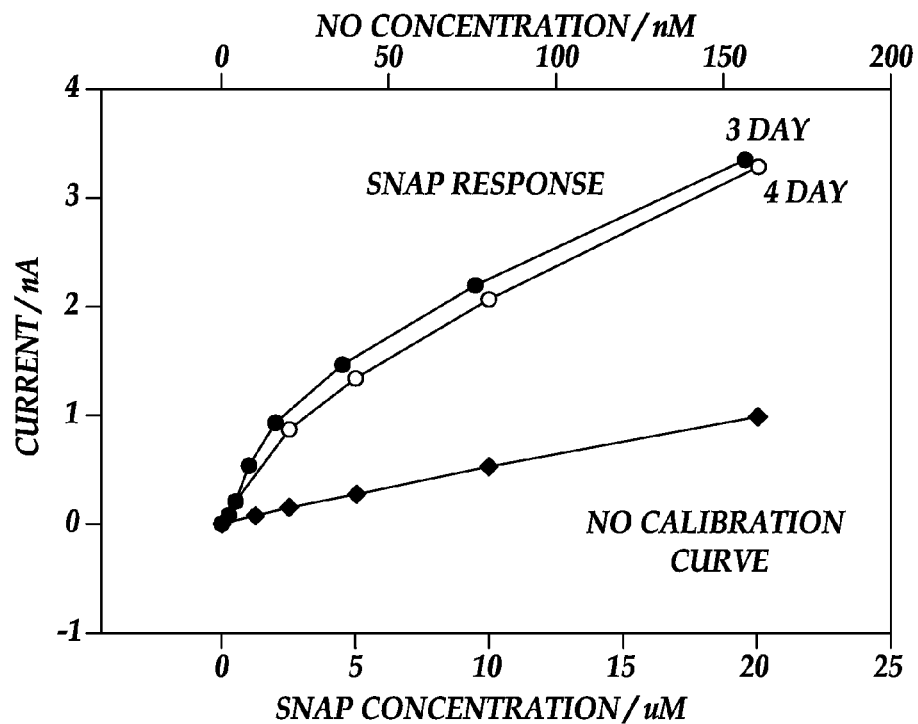
FIG. 11 is a graph of the NO concentration and S-nitroso-N-acetylpenicilamine (SNAP) concentration versus current as detected by an embodiment of the nitrosothiol sensor device of the present disclosure.
Figure 12:
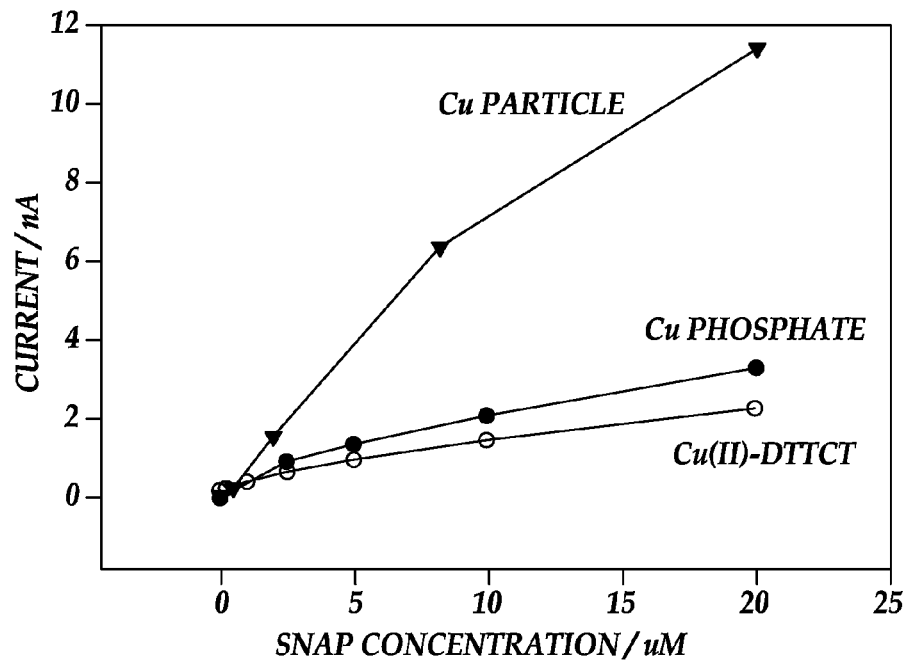
FIG. 12 is a graph of the SNAP concentration versus current as detected by three different embodiments of the nitrosothiol sensor device of the present disclosure.

FIGS. 11 and 12 are graphs illustrating a test that was run to detect SNAP using copper (II) phosphate as the catalyst in the material 124.

Specifically referring to FIG. 11, both the NO concentration and the SNAP concentration are shown as a function of the current supplied by the working electrode 110. Currents were measured at +0.75V vs. Ag/AgCl and in the PBS buffer solution containing 100 mM EDTA and 10 μM Ascorbic acid (sodium salt). As shown in FIG. 11, the nitrosothiol sensor device 100 can measure the SNAP at below about 0.1 μM concentration, due in part to the sensor device's 100 high sensitivity. It is believed, without being bound to any theory, that the high sensitivity of the sensor device 100 may be due in part to the high content of free copper ions (usually Cu(II)) in the material 124. The high content of free copper ions may be due to the corrosion of Cu metal at the surface of the particles in the presence of dissolved oxygen. FIG. 11 also illustrates that the nitrosothiol sensor device 100 may take measurements for as long as 3-4 days after the initial reading.

Referring now to FIG. 12, the concentration of SNAP was measured as a function of the current supplied by the working electrode 110. As previously stated, currents were measured at +0.75V vs. Ag/AgCl and in the PBS buffer solution containing 100 mM EDTA and 10 µM Ascorbic acid (sodium salt). FIG. 12 shows the SNAP concentrations for three different embodiments of the nitrosothiol sensor device 100 of the present disclosure. One of the devices 100 had a Cu particle in polymer coating, one had a Cu phosphate in polymer coating, and the third had a Cu(II) complex (specifically Cu(II)-DTTCT) in polymer coating. All three embodiments of the sensor device 100 detected the SNAP in the sample. FIG. 12 illustrates that the nitrosothiol sensor device's 100 sensitivity may vary depending on the type of copper source used.

The nitrosothiol sensor device 100 of the present disclosure may measure the RSNO concentration in a sample, where the RSNO concentration ranges between about sub-µM and about 40 µM. Further, the nitrosothiol sensor device 100 was found to have a detection limit of about 0.2 µM for SNAP and CysNO and about 0.5 µM for GSNO and SNAC.

It is to be understood that the nitrosothiol sensor device's 100 relatively long-term sensitivity may decrease continuously, due in part to the leaching of the copper source (complexes, compounds, ions) from the material 124 to a solution phase. Further, it is contemplated that the sensor device's 100 sensitivity may also be dependant on the amount of reducing agent in the solution/sample, the type of RSNO species being detected and/or the amount of EDTA present, if any. Still further, it is to be understood that the number of uses of the sensor device 100 may also impact the sensitivity because the stirring condition may facilitate leaching of the catalytic active copper species.

Figure 13:
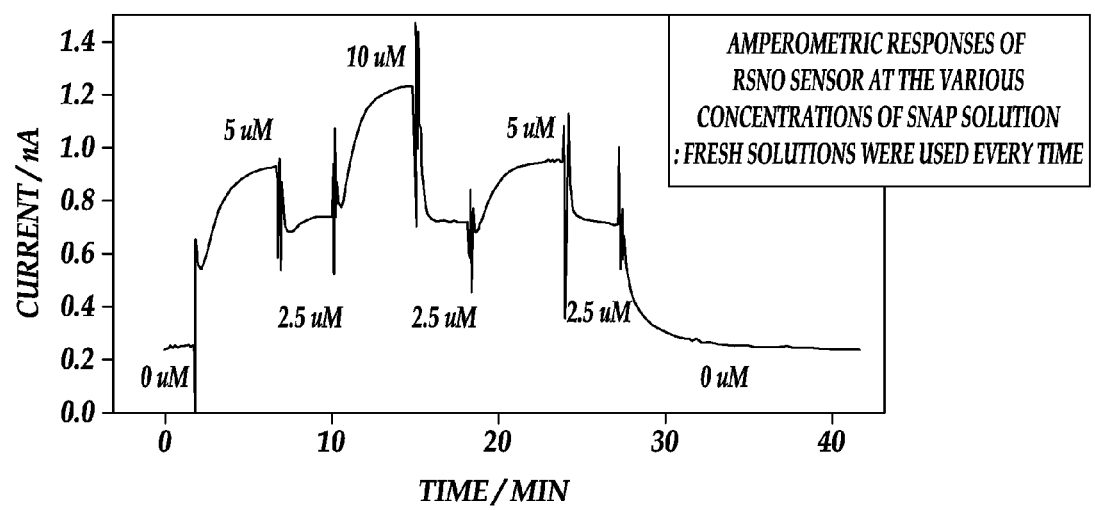
FIG. 13 is a graph showing a sensor signal (current versus time) having a reproducible pattern detected by an embodiment of the nitrosothiol sensor device of the present disclosure.

Further, it is contemplated that the nitrosothiol sensor device 100 of the present disclosure may advantageously remain unclogged due in part to the existence of the copper source in the material 124. It is believed, without being bound to any theory, that the existence of the copper source may also advantageously prolong the sensitivity of the nitrosothiol sensor device 100 such that reading may be reproduced over time (generally a few days). FIG. 13 illustrates the reproducible pattern of measurements taken by the nitrosothiol sensor device 100.

The present disclosure offers many advantages, including, but not limited to the following. An important advantage of the nitrosothiol sensor device 100 over previous sensors for measuring nitrosothiols is that the readings are reproducible for relatively long term use. An important advantage of embodiments of the method for generating NO locally at the surface of polymers or other materials is the potential simplicity of simply dip-coating the material with a material containing a reactive agent. The material may have a single reactive agent or mixture of reductase activities. It may be a biological protein (enzyme), a source of metal/metal ions, or a metal ion ligand complex that mimics the enzyme function.

Even in those embodiments where added $TDMA^+NO_2^-/NO_3^-$ or some other nitrite, nitrate, or nitrosothiol, such as nitroso cysteine, is required and/or desired within the material, the stability of such a species is likely to far exceed the stability of diazeniumdiolates and other NO donors used to date.

In a clinical situation, it should be noted that, even if the amount of reducing equivalent species in the blood were to vary from test subject to test subject, it is possible to add reducing equivalents of an alternate electron donor to the blood, illustratively in the form of ascorbic acid, by administering low doses of Vitamin C to the patient. This may aid in ensuring the presence of adequate levels of reducing equivalents.

While several embodiments of the disclosure have been described in detail, it will be apparent to those skilled in the art that the disclosed embodiments may be modified. Therefore, the foregoing description is to be considered exemplary rather than limiting.

What is claimed is:

1. A device for detecting nitrosothiol content in a solution, the device comprising:
    at least two electrodes disposed in a housing having opposed ends, wherein one of the at least two electrodes is a working electrode having a platinized tip and wherein the other of the at least two electrodes is a counter electrode;
    a glass capillary supported within the housing and protruding beyond one of the opposed ends of the housing, wherein the working electrode is substantially surrounded by the glass capillary, and the counter electrode is connected to the glass capillary within the housing; and
    a filter membrane disposed at an other of the opposed ends of the housing and configured to come in contact with the solution, the filter membrane and at least a portion of the working electrode having a material coated thereon, wherein the material comprises:
        a polymer; and
        a source of copper dispersed within the material;
    wherein the material and the platinized tip are configured to come into contact with the solution containing nitrosothiols to convert the nitrosothiols to nitric oxide in order to detect the nitrosothiol content.

2. The device as defined in claim 1 wherein the polymer is selected from the group consisting of hydrophilic polyurethanes, polytetrafluoroethylene, poly(vinyl chloride), silicon rubbers and mixtures thereof.

3. The device as defined in claim 1 wherein the source of copper comprises at least one of copper particles, copper compounds, copper salts, copper complexes, and mixtures thereof.

4. The device as defined in claim 1 wherein the working electrode comprises platinum wire, and the counter electrode comprises silver wire.

* * * * *